United States Patent [19]
Konishi et al.

[11] 3,961,064
[45] June 1, 1976

[54] PHARMACEUTICAL COMPOSITION FOR REMEDY OF HYPERAMMONIEMIA

[75] Inventors: Toji Konishi, Tokyo; Masanori Kayano, Honjo; Yoshio Tanabe, Fujimi, all of Japan

[73] Assignee: Eisai Co., Ltd., Tokyo, Japan

[22] Filed: Nov. 21, 1974

[21] Appl. No.: 525,744

[30] Foreign Application Priority Data
Nov. 21, 1973 Japan............................... 48-130123

[52] U.S. Cl. ............................................... 424/266
[51] Int. Cl.² ........................................ A61K 31/455
[58] Field of Search .................................... 424/266

[56] References Cited
OTHER PUBLICATIONS

Chemical Abstracts 78:146518g (1973).
Chemical Abstracts 77:14181m (1972).
Chemical Abstracts 69:104963g (1968).
Chemical Abstracts 74:94775j (1971).
Chemical Abstracts 67:105516j (1967).

Primary Examiner—Leonard Schenkman
Attorney, Agent, or Firm—Woodhams, Blanchard and Flynn

[57] ABSTRACT

Warm-blooded animals having hyperammoniemia are treating by administration of a pharmaceutical composition comprising nicotinohydroxamic acid.

6 Claims, No Drawings

PHARMACEUTICAL COMPOSITION FOR REMEDY OF HYPERAMMONIEMIA

BACKGROUND OF THE INVENTION

This invention relates to a pharmaceutical composition comprising nicotinohydroxamic acid and to a method for treating hyperammoniemia in warm-blooded animals by using said composition.

It is known that ammonia is present at an extroardinarily high level in the blood of patients suffering from liver diseases such as hepatocirrhosis. In such cases, a treatment has heretofore been conducted by oral administration of a non-absorptive antibiotic such as neomycin. However, administration of such antibiotic causes such side effects as diarrhoea, bacterial alteration and gastric troubles.

SUMMARY OF THE INVENTION

We have completed this invention based on the finding that administration of nicotinohydroxamic acid reduces the blood-ammonia level in patients having hyperammoniemia and improves the clinical symptons of patients greatly without inviting side effects such as those mentioned above.

It is therefore a primary object of this invention to provide a pharmaceutical composition for treatment of hyperammoniemia which comprises nicotinohydroxamic acid and a pharmaceutically acceptable carrier or diluent.

Another object of this invention is to provide a method for treating hyperammoniemia comprising administering a therapeutically effective amount of nicotinohydroxamic acid to warm-blooded animals having hyperammoniemia.

Other objects of this invention will be apparent from the following detailed description and Examples.

Nicotinohydroxamic acid to be used as the active ingredient in this invention is represented by the following formula:

[Structural formula: pyridine ring with CONHOH substituent]

This compound is a white crystalline powder which tastes slightly bitter and has a melting point of about 160°C (as measured according to the melting point measurement method described at page 851 of the Japanese Pharmacopoeia, 8th edition). It is relatively difficultly soluble in water, methanol and glacial acetic acid and is hardly soluble in ether, acetone, benzene and chloroform.

Nicotinohydroxamic acid can be prepared according to known methods for synthesis of hydroxamic acids. For example, it can easily be prepared by reacting hydroxylamine with an ester, halide (such as chloride), amide or anhydride of nicotinic acid. An example of the preparation of nicotinohydroxamic acid will now be described.

360 g (5 moles) of hydroxylamine hydrochloride is added to a solution of 333 g (8 moles) of NaOH in 1500 ml of water at about 20°C. Then, 360 g (2.6 moles) of methyl nicotinate is added to the resulting transparent solution, and the mixture is agitated at 20°–25°C for 1 hour and 30 minutes. The reaction solution is neutralized to a pH of 7.5 by addition of about 300 ml of concentrated hydrochloric acid. The precipitated crystals are separated by filtration, washed with 300 ml of water and recrystallized from water to obtain a pure product having a melting point of 160°C (decomposition) in a yield of 272 g (74%).

Elementary Analysis Values, $C_6H_6N_2O_2$ (as molecular weight of 138.12):
Calculated: C, 52.17%, H, 4.38%, N, 20.28%. Found: C, 52.08%, H, 4.38%, N, 20.21%.

The excellent effect of nicotinohydroxamic acid for inhibiting the increase of the blood-ammonia level is proven by the results of the following two tests using dogs.

1. Oral Administration Test on Nicotinohydroxamic Acid

In this test, three crossbred dogs (female having a body weight of 13 Kg, male having a body weight pf 12 Kg and male having a body weight of 18.5 Kg) were used. The portal vein of each dog was strangulated by platinum and after passage of 40 days, the test was initiated. Blood was collected (PRE) 30 minutes before initiation of the test, and 2 g/Kg of urea was given to the dog in the state mixed with a dog food. Just after the dog finished eating of this dog food, a gelatin capsule containing 10 mg/Kg of nicotinohydroxamic acid was forcibly administered orally. After administration of nicotinohydroxamic acid, blood was collected every 1 hour. Ammonia level of collected blood samples was determined according to the method of Okuda and Fujii [Modern Medicine Saishinigaku), 21, 622 – 627 (1966)] (present test). The control test was conducted 10 days before or after the present test by using the same dogs (Cross-Over method) in the same manner as in the present test except that administration of capsules of nicotinohydroxamic acid was not effected. Results are shown in Table 1.

From the results shown in Table 1 given below, it will be understood that nicotinohydroxamic acid inhibits greatly the increase of the blood-ammonia level caused by urea load over a period of 3 to 6 hours after administration.

Table 1

| | Female Dog, 15 Kg | | | | Male Dog, 12 Kg | | | |
|---|---|---|---|---|---|---|---|---|
| | $A^1$ | $a^1$ | $B^1$ | $b^1$ | $A^2$ | $a^2$ | $B^2$ | $b^2$ |
| PRE | 165 | | 174 | | 185 | | 166 | |
| 1 Hour | 184 | + 21 | 161 | −13 | 205 | + 20 | 171 | + 5 |
| 2 Hours | 217 | + 54 | 177 | + 3 | 215 | + 30 | 173 | + 7 |
| 3 Hours | 295 | +132 | 187 | +13 | 256 | + 71 | 241 | +75 |
| 4 Hours | 284 | +121 | 264 | +90 | 292 | +107 | 248 | +82 |
| 5 Hours | 276 | +113 | 260 | +86 | 289 | +104 | 255 | +89 |

| | Male Dog, 18.5 Kg | | | | Average of Three Dogs | |
|---|---|---|---|---|---|---|
| | $A^3$ | $a^3$ | $B^3$ | $b^3$ | C | D |
| PRE | 133 | | 166 | | | |
| 1 Hour | 148 | + 15 | 149 | −17 | 18.7 ± 2.6 | −8.3 ± 9.8 |
| 2 Hours | 155 | + 22 | 142 | −24 | 35.3 ± 13.6 | −4.7 ± 13.8 |
| 3 Hours | 229 | + 96 | 142 | −24 | 99.7 ± 25.0 | 21.3 ± 40.8 |
| 4 Hours | 243 | +110 | 186 | +20 | 112.7 ± 6.0 | 64.0 ± 31.3 |
| 5 Hours | 252 | +119 | 199 | +33 | 112.0 ± 6.2 | 69.3 ± 25.7 |

PRE: blood-ammonia level (µg/dl) 30 minutes before administration of urea
$A^1$, $A^2$, $A^3$: blood-ammonia level (µg/dl) in control test
$B^1$, $B^2$, $B^3$: blood-ammonia level (µg/dl) in present test
$a^1$, $a^2$, $a^3$: difference between blood-ammonia level obtained at each measurement in control test and blood-ammonia level of PRE
$b^1$, $b^2$, $b^3$: difference between blood ammonia level obtained at each measurement in present test and blood-ammonia level of PRE
C: average of $a^1$, $a^2$ and $a^3$ obtained at each

Table 1-continued

D : measurement
average of $b^1$, $b^2$ and $b^3$ obtained at each measurement

2. Intravenous Administration Test on Nicotinohydroxamic Acid

In this test, three cross-bred dogs (female having a body weight of 14 Kg, male having a body weight of 13.5 Kg and male having a body weight of 19.5 Kg) were used. The portal vein of each dog was strangulated by platinum and after passage of 40 days, the test was initiated. Blood was collected 30 minutes (PRE 3), 20 minutes (PRE 2) and 10 minutes (PRE 1) before initiation of the test. 300 mg/Kg of physiological saline solution of urea (urea concentration: 500 mg/ml) was intravenously injected into each dog, and blood was collected 10 minutes afer the injection. Immediately, a physiological saline solution of nicotinohydroxamic acid (concentration = 20 mg/ml) was intravenously injected and blood was collected every 10 or 30 minutes. Ammonia level of collected blood samples was determined by the method of Okuda and Fujii (see the above reference) (present test). The control test was conducted 10 days before or after the present test by using the same dogs (Cross-Over method) in the same manner as in the present test except that the intravenous injection of nicotinohydroxamic acid was not effected. Results are shown in Table 2.

From the results shown in Table 2 given below, it will readily be understood that when urea is intravenously administered into dogs, the blood-ammonia level immediately increases but this increase is greatly inhibited by administration of nicotinohydroxamic acid.

Table 2

| | Female Dog, 14 Kg | | | | Male Dog, 13.5 Kg | | | |
|---|---|---|---|---|---|---|---|---|
| | $E^1$ | $e^1$ | $F^1$ | $f^1$ | $E^2$ | $e^2$ | $F^2$ | $f^2$ |
| PRE 3 | 150 | | 156 | | 168 | | 169 | |
| PRE 2 | 145 | | 153 | | 170 | | 162 | |
| PRE 1 | 148 | | 153 | | 169 | | 163 | |
| PRE A | 148 | | 154 | | 169 | | 165 | |
| 10 minutes | 189 | +41 | 185 | +31 | 192 | +23 | 196 | +31 |
| 20 minutes | 198 | +50 | 200 | +46 | 224 | +55 | 238 | +73 |
| 30 minutes | 209 | +61 | 169 | +15 | 231 | +62 | 187 | +22 |
| 40 minutes | 195 | +47 | 163 | + 9 | 212 | +43 | 160 | − 5 |
| 50 minutes | 186 | +38 | 177 | +23 | 201 | +32 | 160 | − 5 |
| 60 minutes | 174 | +26 | 188 | +34 | 186 | +17 | 163 | − 2 |
| 70 minutes | 180 | +32 | 187 | +33 | 190 | +21 | 166 | + 1 |
| 89 minutes | 205 | +57 | 201 | +47 | 179 | +10 | 164 | − 1 |
| 100 minutes | 181 | +33 | 184 | +30 | 173 | + 4 | 164 | − 1 |
| 120 minutes | 187 | +39 | 183 | +29 | 180 | +11 | 158 | − 7 |
| 150 minutes | 176 | +28 | 175 | +21 | 186 | +17 | 152 | −13 |
| 180 minutes | 162 | +14 | 168 | +14 | 187 | +18 | 157 | − 8 |

| | Male Dog, 19.5 Kg | | | | Average of Three Dogs | |
|---|---|---|---|---|---|---|
| | $E^3$ | $e^3$ | $F^3$ | $f^3$ | G | H |
| PRE 3 | 148 | | 148 | | | |
| PRE 2 | 151 | | 150 | | | |
| PRE 1 | 153 | | 147 | | | |
| PRE A | 151 | | 148 | | | |
| 10 minutes | 195 | +44 | 187 | +39 | 36.0 ± 9.3 | 33.7 ± 3.8 |
| 20 minutes | 200 | +49 | 185 | +37 | 51.3 ± 2.6 | 52.0 ± 15.3 |
| 30 minutes | 219 | +68 | 187 | +39 | 63.7 ± 3.1 | 25.3 ± 10.1 |
| 40 minutes | 197 | +46 | 167 | +19 | 45.3 ± 1.7 | 7.7 ± 9.8 |
| 50 minutes | 198 | +47 | 163 | +15 | 39.0 ± 1.2 | 11.0 ± 11.8 |
| 60 minutes | 206 | +55 | 164 | +16 | 32.7 ± 16.2 | 16.0 ± 14.7 |
| 70 minutes | 188 | +37 | 166 | +18 | 30.0 ± 6.7 | 7.3 ± 5.6 |
| 89 minutes | 179 | +28 | 158 | +10 | 31.7 ± 19.4 | 18.7 ± 20.6 |
| 100 minutes | 170 | +19 | 160 | +12 | 18.7 ± 11.8 | 13.7 ± 12.7 |
| 120 minutes | 168 | +17 | 167 | +19 | 22.3 ± 12.0 | 13.7 ± 15.2 |
| 150 minutes | 169 | +18 | 164 | +16 | 21.0 ± 5.0 | 8.0 ± 15.0 |
| 180 minutes | 163 | +12 | 145 | − 3 | 14.7 ± 2.5 | 1.0 ± 9.4 |

PRE 3: blood-ammonia level (μg/dl) 30 minutes before administration of urea

Table 2-continued

| | |
|---|---|
| PRE 2: | blood-ammonia level (μg/dl) 20 minutes before administration of urea |
| PRE 1: | blood-ammonia level (μg/dl) 10 minutes before administration of urea |
| PRE A: | average of PRE 3, PRE 2 and PRE 1 |
| $E^1$, $E^2$, $E^3$: | blood-ammonia level (μg/dl) in control test |
| $F^1$, $F^2$, $F^3$: | blood-ammonia level (μg/dl) in present test |
| $e^1$, $e^2$, $e^3$: | difference between blood-ammonia level obtained at each measurement in control test and blood-ammonia level of PRE A |
| $f^1$, $f^2$, $f^3$: | difference between blood-ammonia level obtained at each measurement in present test and the blood-ammonia level of PRE A |
| G : | average of $e^1$, $e^2$ and $e^3$ obtained at each measurement |
| H : | average of $f^1$, $f^2$ and $f^3$ obtained at each measurement |

The acute toxicity (LD50) observed when nicotinohydroxamic acid of this invention is administered to rats and mice by several administration methods is shown in Table 3.

Table 3

| Administration | | Rats (mg/Kg) | Mice (mg/Kg) |
|---|---|---|---|
| Oral administration | male | 1024 | 1950 |
| | female | 1490 | 1510 |
| Intraperitoneal administration | male | 590 | 1500 |
| | female | 740 | 1100 |

Each value shown in Table 3 is an average value obtained by conducting the test by using a group consisting of 5 rats or mice.

The pharmaceutical composition of this invention can contain about 10 to about 50 mg in an administration unit form such as a tablet, a coated tablet, a capsule or a syrup. A solid preparation can include an ordinary pharmaceutical carrier such as lactose, sucrose, sorbitol, mannitol, starch, a cellulose derivative, calcium or magnesium stearate, carbon wax, PVP, etc. An aqueous preparation for oral administration can contain, if desired, a pharmaceutical diluent, for example, a dissolution assistant such as nicotinic acid amide, a flavoring agent such as sucrose, a stabilizer, a perfume, a coloring agent, etc. An aqueous preparation for injection comprises nicotinohydroxamic acid and distilled water for injection, and according to need, it may further comprise a pharmaceutical diluent such as a dissolution assistant, a stabilizer or other adjuvant. These pharmaceutical preparations can easily be formed according to techniques well-known in the art.

The amount of the composition to be used for treatment can be varied depending on the disease condition of a patient, but in the case of adults, the composition is generally administered in an amount as nicotinohydroxamic acid of 200 to 2400 mg per day, preferably 600 to 1200 mg per day. It is recommended to administer the composition 3 to 4 times per day.

Examples of pharmaceutical preparations suitable for administration of the active compound of this invention will now be illustrated.

Example 1

Tablet:

| | mg in one tablet |
|---|---|
| nicotinohydroxamic acid | 200 |
| lactose | 67.7 |

-continued

| | mg in one tablet |
|---|---|
| microcrystalline cellulose (Avicel) | 35.0 |
| corn starch | 17.5 |
| carboxymethyl cellulose | 10.5 |
| PVP (K-50) | 17.5 |
| calcium stearate | 1.8 |
| total | 350 |

Nicotinohydroxamic acid, lactose, microcrystalline cellulose, corn starch and carboxymethyl cellulose are mixed sufficiently, and an aqueous solution of PVP (K-30) is added as a binder. Granules are prepared from the mixture according to customary procedures, and calcium stearate as a lubricant is incorporated and mixed in the granules. Then, the granules are formed into tablets, each having a weight of 350 mg.

Example 2

Enterically Coated Tablet:

Films are formed on the surfaces of tablets prepared according to the method of Example 1 by using an acetone solution of cellulose acetate phthalate according to customary procedures.

Example 3

Injection Solution:

| | mg in one ampoule |
|---|---|
| nicotinohydroxamic acid | 125 |
| distilled water for injection | balance |
| total | 10 ml |

Nicotinohydroxamic acid is dissolved in distilled water for injection, and the solution is filtered and 10 ml of the solution is filled into each ampoule. The ampoules are melt-sealed and sterilized.

Example 4

Injection Solution:

| | mg in one ampoule |
|---|---|
| nicotinohydroxamic acid | 350 |
| nicotinic acid amide | 500 |
| distilled water for injection | balance |
| total | 10 ml |

Nicotinohydroxamic acid and nicotinic acid amide (dissolution assistant) are added to ⅓ (by volume) of distilled water for injection, and the remaining ⅔ of distilled water for injection is gradually added to the mixture to dissolve the components in water. The solution is filtered, and 10 ml of the solution is filled in each ampoule. The ampoules are melt-sealed and sterilized.

Example 5

Syrup for Oral Administration:

| | g in 100 ml of syrup |
|---|---|
| nicotinohydroxamic acid | 1.0 |
| nicotinic acid amide | 2.0 |
| methyl cellulose | 0.5 |
| white sugar | 3.0 |
| distilled water | balance |
| total | 100 ml |

Methyl cellulose is dissolved in about ⅓ (by volume) of water. Separately, nicotinohydroxamic acid and nicotinic acid amide are dissolved in about ⅔ (by volume) of water, and white sugar is added thereto and the mixture is heated to dissolve the components in water. The so formed solution is cooled and mixed with the above aqueous solution of methyl cellulose. The resulting syrup is, if necessary, diluted with distilled water so that the amount of water reaches the prescribed level.

Example 6

Capsule:

| | mg in one capsule |
|---|---|
| nicotinohydroxamic acid | 200 |
| lactose | 100 |

The above components are mixed homogeneously, and the mixture is filled in hard capsules of gelatin.

Results of the clinical test in which pharmaceutical preparations of this invention containing nicotinohydroxamic acid were administered to 13 patients having hyperammoniemia based on liver trouble will now be described.

| Patient No. | Sex | Age | Disease |
|---|---|---|---|
| 1 | male | 43 | hepatocirrhosis |
| 2 | male | 49 | hepatocirrhosis, liver cancer |
| 3 | female* | 49 | hepatocirrhosis |
| 4 | female* | 53 | hepatocirrhosis |
| 5 | male* | 57 | hepatitis |
| 6 | male* | 50 | hepatocirrhosis |
| 7 | female | 51 | hepatocirrhosis |
| 8 | male* | 27 | hepatitis acute by poison, syphilis |
| 9 | male | 39 | hepatocirrhosis |
| 10 | female* | 59 | hepatocirrhosis |
| 11 | male | 48 | hepatocirrhosis |
| 12 | female | 52 | hepatocirrhosis |
| 13 | female* | 72 | hepatocirrhosis |

*patients who had experienced the coma or pre-coma state in the past or just before administration Tablets containing 200 mg of nicotinohydroxamic acid (hereinafter abbreviated to "NTX-N"), which were prepared according to the method of Example 1, were administered to patients Nos. 1 to 7. Enterically coated tablets containing 200 mg of nicotinohydroxamic acid, which were prepared according to the method of Example 2, were administered to patients Nos. 8 to 13. The daily dose was appropriately arranged within a range of from 3 to 6 tablets (600 mg to 1200 mg), and the tablets were administered dividedly, namely 3 times in a day, regardless of whether the administration was before or after meals. The administration period was changed depending on the patients, and the shortest period was 4 days and the longest period was 60 days, the average administration period among these 13 patients being 26 days.

With respect to each patient, blood was collected just after administration and 4 days after administration, and further, blood was collected several times every 4 to 7 days before or after administration. Each of the collected blood samples were tested to determine the blood-ammonia level according to the above-mentioned method of Okuda and Fujii.

Results of measurement of blood-ammonia levels before and after administration of nicotinohydroxamic acid are shown in Table 4, data of the average blood-ammonia levels before and after the administration are shown in Table 5, and data of average blood-ammonia levels just before the administration and 4 days after the administration are shown in Table 6.

Table 4

| Patient No. | Blood-Ammonia Level (μg/dl) before administration | | | | | | | | average |
|---|---|---|---|---|---|---|---|---|---|
| 1 | | | | | | 150 | 143 | | 147 |
| 2 | | | | | | 233 | 189 | | 261 |
| 3 | | | | | | 275 | 244 | | 260 |
| 4 | | | | | 272 | 194 | 197 | | 221 |
| 5 | | | | | | 275 | 327 | | 301 |
| 6 | | 265 | 132 | 152 | 171 | 207 | 253 | | 197 |
| 7 | | | | | 202 | 255 | 243 | | 233 |
| 8 | | | | | 283 | 215 | 223 | | 240 |
| 9 | | | | | | | 126 | | 126 |
| 10 | | | | | 166 | 119 | 211 | | 165 |
| 11 | | | | | | 135 | 149 | | 142 |
| 12 | | | | | | | 219 | | 219 |
| 13 | | 205 | 218 | 201 | 196 | 208 | 252 | 260 | 220 |

| Patient No. | after administration | | | | | | | | average |
|---|---|---|---|---|---|---|---|---|---|
| 1 | 83 | 89 | | | | | | | 86 |
| 2 | 201 | 251 | 130 | | | | | | 194 |
| 3 | 178 | 159 | 166 | 164 | 136 | 133 | 108 | 146 218 | 156 |
| 4 | 150 | 124 | 195 | | | | | | 156 |
| 5 | 145 | 280 | | | | | | | 213 |
| 6 | 153 | 149 | 168 | 148 | 122 | | | | 148 |
| 7 | 168 | 144 | 138 | | | | | | 150 |
| 8 | 189 | 115 | 121 | 117 | | | | | 136 |
| 9 | 92 | 77 | | | | | | | 85 |
| 10 | 193 | 196 | | | | | | | 195 |
| 11 | 109 | 200 | | | | | | | 155 |
| 12 | 182 | | | | | | | | 182 |
| 13 | 254 | 201 | 167 | 230 | 256 | 105 | 167 | | 197 |

Notes:
1) The most right value in column "before administration" is a value obtained just before administration.
2) The most left value in column "after administration" is a value obtained 4 days after administration.

| | remarks about consciousness (troubles in consciousness) | | electroencephalogram | effect |
|---|---|---|---|---|
| | before administration | after administration | | |
| 1 | one or two fits per week | no fit | improved | remarkably effective |
| 2 | trouble in consciousness once or twice per day | trouble in consciousness reduce to once per day | slightly improved | effective |
| 3 | trouble in consciousness once or twice per day | lucid slight trouble in consciousness | slightly improved | remarkably effective |
| 4 | pre coma incontinence | lucid the incontinence vanished | improved | remarkably effective |
| 5 | exhausted, feeling of fatigue pre coma syndrome | unchanged | unchanged | not effective |
| 6 | diarrhoea troubles in consciousness three times per week | no pre-coma during administration | slightly improved | effective |
| 7 | exhausted inappetence abdominal inflation | the abdominal inflation vanished | — | remarkably effective |
| 8 | post coma syndrome trouble in consciousness | no coma, no fit | unchanged | not effective |
| 9 | exhausted inappetance | unchanged | — | not effective |
| 10 | exhausted feeling of fatigue | the trouble in consciousness vanished | improved | effective |
| 11 | exhausted nausea pre-coma | unchanged | unchanged | not effective |
| 12 | exhausted inappetence coma syndrome | recovery of consciousness | slightly improved | effective |
| 13 | pre coma troubles in consciousness | improved in trouble in consciousness | slightly improved | effective |

Table 5

| | Before Administration | After Administration |
|---|---|---|
| Number of Patients | 13 | 13 |
| Average Blood-Ammonia Level (μg/dl) | 210.15 | 157.92 |
| Standard Deviation | 52.41 | 39.75 |

Table 6

| | Just Before Administration | 4 Days After Administration |
|---|---|---|
| Number of Patients | 13 | 13 |
| Average Blood-Ammonia Level (μg/dl) | 221.38 | 160.92 |
| Standard Deviation | 57.80 | 46.71 |

With respect to values shown in Tables 5 and 6, the t test of hypothesis of the difference between the average values and the corresponding t test of hypothesis were conducted to obtain results of $p = 0.01$ and $p = 0.001$, respectively. Accordingly, it was confirmed that nicotinohydroxamic acid of this invention reduces the blood-ammonia level with a significant difference.

What is claimed is:

1. A method of lowering the blood-ammonia level in humans suffering from liver disease and having hyperammoniemia as a consequence thereof, which comprises:

administering to such a human from 200 to 2400 mg per day of nicotinohydroxamic acid in the form of divided doses of a therapeutic composition containing nicotinohydroxamic acid with a pharmaceutically acceptable carrier, diluent or vehicle.

2. A method as claimed in claim 1 in which from 600 to 1200 mg per day of nicotinohydroxamic acid is administered to said human in the form of divided doses administered 3 to 4 times a day.

3. A method as claimed in claim 1 wherein the nicotinohydroxamic acid is administered orally.

4. A method as claimed in claim 1 wherein the nicotinohydroxamic acid is administered in injection.

5. A method as claimed in claim 1 in which the human suffers from hepatocirrhosis.

6. A method as claimed in claim 1 in which the human suffers from hepatitis.

* * * * *